United States Patent [19]

Bowden et al.

[11] Patent Number: 5,073,028
[45] Date of Patent: Dec. 17, 1991

[54] SCANNING DENSITOMETER

[75] Inventors: David R. Bowden; Ross A. Ouwinga, both of Grand Rapids; Lawrence D. Zandstra, Rockford, all of Mich.

[73] Assignee: X-Rite, Incorporated, Grandville, Mich.

[21] Appl. No.: 512,856

[22] Filed: Apr. 23, 1990

[51] Int. Cl.$^5$ .............................................. G01J 3/51
[52] U.S. Cl. ................... 356/402; 356/406; 356/407; 364/526
[58] Field of Search ................ 356/73, 402, 404, 406, 356/418, 419, 425, 443, 444, 446, 407; 364/526

[56] References Cited

U.S. PATENT DOCUMENTS

| 3,795,958 | 12/1976 | Pfahl et al. | 356/402 |
| 3,995,958 | 12/1976 | Pfahl et al. | 356/402 |
| 4,003,660 | 1/1977 | Christie | 356/416 |
| 4,289,405 | 9/1981 | Tobias | 356/402 |
| 4,505,589 | 3/1985 | Ott et al. | 356/402 |
| 4,591,978 | 5/1986 | Peterson et al. | 364/200 |

OTHER PUBLICATIONS

Gretag Brochure Entitled Scanning Densitometer D732.
Cosar Corporation Brochure Entitled The Autosmart Densitometer (Copyright 1985).
Tobias Associates, Inc. brochure relating to the Tobias SCR Scanning Densitometer.
Graphometronic brochure relating to APS 400.

Primary Examiner—F. L. Evans
Assistant Examiner—K. P. Hantis
Attorney, Agent, or Firm—Varnum, Riddering, Schmidt & Howlett

[57] ABSTRACT

A scanning densitometer is disclosed for obtaining color density measurements from colored samples, such as color bars and the like. The scanning densitometer includes a densitometer head (100) and a densitometer head transport system (101) having transport bars (102, 103). A sample sheet is positioned under the transport bars (102, 103) and the self-propelled head (100) moves over the sheet along the bars (102, 103) toward an end limit stop (105). During a return movement from the end limit stop (105) to a docking end housing (110), color measurement data is obtained. Upon docking at the docking end housing (110), an optical communications interface is provided so that data from the densitometer head (100) can be transmitted to a host computer.

19 Claims, 8 Drawing Sheets

SCANNING DENSITOMETER

BACKGROUND OF THE INVENTION

1. Field of the Invention

The invention relates to apparatus and methods associated with color measurement and analysis technology and, more particularly, to apparatus and methods for automated color density measurements of color "control bars" and the like obtained during a scanning procedure.

2. Description of Related Art

It is well known that the term "color" as applied to electromagnetic radiation represents in part the relative energy distribution of radiation within the visible spectrum. That is, light providing a stimulus to the human eye, and having a particular energy distribution, may be perceived as a substantially different color than light of another energy distribution. Concepts relating to the characteristics of color and light waves are the subject of numerous well-known texts, such as *Principles of Color Technology*, Meyer, Jr. and Saltzman (Wiley 1966), and *The Measurement of Appearance*, Hunter and Harold (Wiley 2nd Ed. 1987).

In recent years, the capability of maintaining the "quality" of color has been of significant importance in various industries, such as, for example, the fields of graphic arts, photography and color film processing. For purposes of performing sample testing and other activities in furtherance of maintaining color quality, it is necessary to first determine an appropriate means for "measuring" and "describing" color. A substantial amount of research has been performed during the past fifty years with respect to appropriate methods and standards for color measurement and description.

For purposes of describing color, and from a purely "physical" point of view, the production of color requires three things: a source of light; an object to be illuminated; and, a means for perceiving the color of the object. The means for perceiving the color can be the human eye and brain or, alternatively, electrical and electromechanical apparatus such as a photosensitive detector and associated auxiliary devices utilized for detecting light. In general, it is desirable to provide a means for measuring color so as to assess the manner in which an image will appear to a human observer, or the manner in which an image will perform in a photographic or other type of reproduction printing operation.

Although human perception and interpretation of color can be useful, reliance on such perception and interpretation can be highly subjective. That is, human nature may cause one person's perception of the color of a particular object to be substantially different from the perception of another. In addition, eye fatigue, age and other physiological factors can influence color perception. Further, visual human perception is often insufficient for color description. For example, certain object samples may be visually perceived under one light source as substantially "matching", and yet may actually have very different spectral characteristics and may be perceived as "nonmatching" under another light source. In view of the foregoing, it is desirable to employ color measurement and description techniques which are objective in nature, and capable of differentiating among object samples having different color characteristics.

Various devices have been developed and are widely utilized to measure and quantitatively describe color characteristics of object samples. Many of these devices provide measurements related to the spectral characteristics of the samples. Described simplistically, when light is directed onto an object sample to be measured for color, the object may absorb a portion of the light energy, while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or reflective materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light. Instruments utilized for generating such spectral characteristics curves are typically referred to as spectrophotometers.

In accordance with conventional optical physics, it is known that the proportion of light incident to an object sample and absorbed by such a sample is independent of the light intensity. Accordingly, a quantitative indication of the spectral characteristics of an object sample can be defined as the "transmittance" or "reflectance" of the sample. That is, the transmittance of a substantially transparent object can be defined as the ratio of power transmitted over light power incident to the sample. Correspondingly, for a reflective object sample, the reflectance can be defined as the ratio of power reflected from the object over the incident light power.

For collimated light, these ratios can be expressed in terms of intensities, rather than power. Furthermore, because of the nature of transmittance/reflectance and the optical characteristics of the human eye, it is advantageous to express these ratios in logarithmic form. Accordingly, one parameter widely used in the field of color technology for obtaining a quantitative measurement or "figure of merit" is typically characterized as optical "density." The optical density of an object sample is typically defined as follows:

$$\text{Optical Density} = D = -\log_{10} T \text{ or } -\log_{10} R \quad \text{(Equation 1)}$$

where T represents transmittance of a transparent object and R represents reflectance of a reflective object. In accordance with the foregoing, if an object sample absorbed 90% of the light incident upon the sample, the reflectance would ideally be 10%. The density of such a sample would then be characterized as unity. Correspondingly, if 99.9% of the light were absorbed, the reflectance would be 0.1% and the density would be 3. Similarly, the density of an "ideal" object reflecting 100% of the light incident upon the object would be 0.

To provide a relative measurement of color, it is possible to utilize the principles of optical density, without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a particular "patch" of a color "control bar" conventionally employed in the printing and graphic arts industries. Density measurements provide a means to assess the manner in which an image will appear to a human observer, or the way an image will perform in a film processing operation. Density measurements can be utilized to produce sensitometric curves to evaluate various printing and reproduction characteristics, as well as utilization to control various photographic operations, such as film processing.

For purposes of measuring optical densities, it is well known to employ a device typically characterized as a "densitometer." These densitometers are often categorized as either "reflection" densitometers, employed for optical density measurements of reflective objects, or are otherwise characterized as "transmission" densitometers. Transmission densitometers are employed for determining spectral characteristics of various light transmitting materials.

Densitometers are utilized in various industries for performing a variety of functions. For example, densitometers can be conveniently employed in printing and graphic arts applications. Processes associated with these applications will be described in greater detail in subsequent paragraphs herein.

To assist in describing the principles of densitometer apparatus, in which certain concepts of the present invention may be employed, FIG. 1 illustrates a simplified schematic representation of a known reflection densitometer configuration 1. Densitometer apparatus of the type shown in FIG. 1 are characterized as reflection densitometers, and utilized to provide color density measurements of reflection materials as previously described.

Referring specifically to FIG. 1, and to numerical references therein, the densitometer apparatus 1 includes a light source unit 2 having a source light 4. With respect to optical density measurements in printing, color film processing, and other industrial fields, various standards have been developed for densitometer light source illuminants. For example, densitometer light source standards have previously been described in terms of a tungsten lamp providing an influx from a lamp operating at a Planckian distribution of 3000° K. Other suggested standards have been developed by the American National Standards Institute ("ANSI") and the International Organization for Standardization ("ISO"). These source light densitometer standards are typically defined in terms of the spectral energy distribution of the illuminant. The source light 4 preferably conforms to an appropriate standard and can, for example, comprise a filament bulb meeting a standard conventionally known in the industry as 2856K ANSI. Power for the source light 4 and other elements of the densitometer apparatus 1 can be provided by means of conventional rechargeable batteries or, alternatively, interconnection to AC utility power for many known densitometers.

The source light 4 projects light through a collimating lens 6 which serves to focus the electromagnetic radiation from the source light 4 into a narrow collimated beam of light rays. Various types of conventional and well-known collimating lenses can be employed. The light rays transmitted through the collimating lens 6 project through an aperture 8 The dimensions of the aperture 8 will determine the size of the irradiated area of the object sample under test.

Various standards have been defined for preferable sizes of the irradiated area. Ideally, the aperture 8 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of the color bar or color patch area to be measured, and is also sized so as to reduce stray light.

The light rays emerging from the aperture 8 (illustrated as rays 10 in FIG. 1) are projected onto the irradiated area surface of an object sample 12 under test. The sample 12 may be any of numerous types of colored reflective materials. For example, in the printing industry, the sample 12 may be an ink-on-paper sample comprising a portion of a color bar at the edge of a color printing sheet. Alternatively, the sample 12 may be a control strip employed in the color film processing industry.

As the light rays 10 are projected onto the object sample 12, electromagnetic radiation shown as light rays 14 will be reflected from the sample 12. Standard detection configurations have been developed, whereby reflected light is detected at a specific angle relative to the illumination light rays 10 projected normal to the plane of the object sample 12. More specifically, standards have been developed for detection of reflected light rays at an angle of 45° to the normal direction of the light rays 10. This angle of 45° has become a standard for reflectance measurements, and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 16 is provided. The filter apparatus 16 can include a series of filters 18, 20 and 22. The filters 18, 20 and 22 are employed for purposes of discriminating the red, green and blue spectral responses, respectively. To more fully explain, red light is absorbed by a cyan ink, thereby providing a cyan color appearance to the observer. Correspondingly, green light is absorbed by a magenta ink, while blue light is absorbed by a yellow ink. Further, each of the filters will tend to absorb light energy at frequencies outside of the bandwidth representative of the particular color hue of the filter. For example, the red filter 18 for cyan indication will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or color reflectance is dependent in substantial part on the spectral transmittance characteristics of the filters. Accordingly, various well-known standards have been developed with respect to spectral characteristics of densitometer filters. For example, one standard for densitometer filters is known as the ANSI status T color response. The spectral response characteristics of filters meeting this standard are relatively wide band (in the range of 50-60 namometers (nms) bandwidth) for each of the cyan, magenta and yellow color hues. Other spectral response characteristic standards include, for example, what is known as G-response, which is similar to status T, but is somewhat more sensitive to respect to yellow hues. An E-response represents a European response standard.

Although the filters 18, 20 and 22 are illustrated in the embodiment shown in FIG. 1 as the cyan, magenta and yellow color shades, other color shades can clearly be employed. These particular shades are considered somewhat preferable in view of their relative permanence, and because they comprise the preferred shades for use in reflection densitometer calibration. However, it is apparent that different shades of red, green and blue, or cyan, magenta and yellow, as well as entirely different colors, can be utilized with the densitometer apparatus 1.

The spectral filters 18, 20 and 22 may not only comprise various shades of color, but can also be one of a number of several specific types of spectral response filters. For example, the filters can comprise a series of conventional Wratten gelatin filters and infrared glass. However, various other types of filter arrangements can also be employed.

The spectral filters 18, 20 and 22 are preferably positioned at a 45° angle relative to the normal direction from the plane of the object sample 12 under test. In the particular example shown in FIG. 1, each of these filters is utilized to simultaneously receive light rays reflected from the object sample 12. Further, although the particular example illustrated in FIG. 1 may include a stationary object sample 12 and stationary apparatus 1, the example embodiment of a densitometer apparatus employing principles of the invention as described in subsequent paragraphs herein can comprise a series of stationary object samples (in the form of a color control bar) with movement of the densitometer apparatus so as to "scan" the object samples. In this type of arrangement, the spectral filter arrangement is continuously moving during color measurements of the object samples. In other known densitometers, the spectral filter measurements may be obtained in sequence, rather than simultaneously, and with or without relative movement of the object samples and densitometer apparatus.

As further shown in FIG. 1, the portion of the reflected light rays 14 passing through the filters 18, 20 and 22 (shown as light rays 24, 26 and 28, respectively) impinge on receptor surfaces of photovoltaic sensor cells. The sensor cells are illustrated in FIG. 1 as sensors 32, 34 and 36 associated with the spectral filters 18, 20 and 22, respectively. The sensors 32, 34 and 36 can comprise conventional photoelectric elements adapted to detect light rays emanating through the corresponding spectral filters. The sensors are further adapted to generate electrical currents having magnitudes proportional to the intensities of the sensed light rays. As illustrated in FIG. 1, electrical current generated by the cyan sensor 32 in response to the detection of light rays projecting through the filter 18 is generated on line pair 38. Correspondingly, electrical current generated by the magenta sensor 34 is applied to the line pair 40, while the electrical current generated by the yellow sensor 36 is applied as output current on line pair 42. Photoelectric elements suitable for use as sensors 36, 38 and 40 are wellknown in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 12, and the spectral response curve of the corresponding filter. Accordingly, for a particular color shade represented by the spectral response curve of the filter, the magnitude of the electrical current represents a quantitative measurement of the proportional reflectance of the object sample 12 within the frequency spectrum of the color shade.

As further shown in FIG. 1, the sensor current output on each of the line pairs 38, 40 and 42 can be applied as an input signal to one of three conventional amplifiers 44, 46 and 48. The amplifier 44 is responsive to the current output of cyan sensor 32 on line pair 38, while amplifier 46 is responsive to the sensor current output from magenta sensor 34 on line pair 40. Correspondingly, the amplifier 48 is responsive to the sensor current output from yellow sensor 36 on line pair 42. Each of the amplifiers 44, 46 and 48 provides a means for converting low level output current from the respective sensors on the corresponding line pairs to voltage level signals on conductors 50, 52 and 54, respectively. The voltage levels of the signals on their respective conductors are of a magnitude suitable for subsequent analog-to-digital (A/D) conversion functions. Such amplifiers are well known in the circuit design art, and are commercially available with an appropriate volts per ampere conversion ratio, bandwidth and output voltage range. The magnitudes of the output voltages on lines 50, 52 and 54 again represent the intensities of reflected light rays transmitted through the corresponding spectral filters.

Each of the voltage signal outputs from the amplifiers can be applied as an input signal to a conventional multiplexer 56. The multiplexer 56 operates so as to time multiplex the output signals from each of the amplifiers 44, 46 and 48 onto the conductive path 58. Timing for operation of the multiplexer 56 can be provided by means of clock signals from master clock 60 on conductive path 62. During an actual density measurement of an object sample, the densitometer 1 will utilize a segment of the resultant multiplexed signal which sequentially represents a voltage output signal from each of the amplifiers 44, 46 and 48.

The resultant multiplexed signal generated on the conductive path 58 is applied as an input signal to a conventional A/D converter 64. The A/D converter 64 comprises a means for converting the analog multiplexed signal on conductor 58 to a digital signal for purposes of subsequent processing by central processing unit (CPU) 66. The A/D converter 64 is preferably controlled by means of clock pulses applied on conductor 68 from the master clock 60. The clock pulses operate as "start" pulses for performance of the A/D conversion. The A/D converter 64 can be any suitable analog-to-digital circuit well known in the art and can, for example, comprise 16 binary information bits, thereby providing a resolution of 65 K levels per input signal.

The digital output signal from the A/D converter 64 can be applied as a parallel set of binary information bits on conductive paths 70 to the CPU 66. The CPU 66 can provide several functions associated with operation of the densitometer apparatus 1. The CPU 66 can be utilized to perform these functions by means of digital processing and computer programs. In addition, the CPU 66 can be under control of clock pulses generated from the master clock 60 on path 72. However, a number of the functional operations of CPU 66 could also be provided by means of discrete hardware components.

In part, the CPU 66 can be utilized to process information contained in the digital signals from the conductive paths 70. Certain of this processed information can be generated as output signals on conductive path 76 and applied as input signals to a conventional display circuit 78. The display circuit 78 provides a means for visual display of information to the user, and can be in form of any one of several well-known and commercially-available display units. However, in an embodiment of a scanning densitometer in accordance with the invention as described in subsequent paragraphs herein, a display unit may not be directly associated with the densitometer apparatus, but instead color measurement data may be transmitted from a densitometer-based processor to another computer system, where the other computer system includes means for analyzing and/or displaying or printing data associated with the color measurements.

In addition to the CPU 66 receiving digital information signals from the conductive paths 70, information signals can also be manually input and applied to the CPU 66 by means of a manually-accessible keyboard circuit 80. The user can supply "adjustments" to color responses and various data parameters by means of entering information through the keyboard 80. Signals representative of the manual input from the keyboard 80 can be applied as digital information signals to the CPU 66 by means of conductive path 82. Again, however, in an embodiment of a scanning densitometer in accordance with the invention as described in subsequent paragraphs herein, a keyboard or similar data entry device may not be directly associated with the densitometer-based processor. Instead, data input to the densitometer apparatus may be provided by data entry devices associated with separate and/or remote computer systems having a communications interface with the densitometer apparatus 1. Concepts associated with providing a communications interface between a densitometer-based computer and an external or remote computer system are disclosed in Peterson et al, U.S. Pat. No. 4,591,978 issued May 27, 1986.

The previously described concepts of densitometry and densitometer apparatus in general can be of primary significance in various industries, including the printing and graphic arts industries. For example, densitometers conventionally known as "scanning" densitometers are typically utilized for analysis of color control bars printed on press sheets so as to analyze the color printing and reproduction, and ensure maintenance of color quality. More specifically, known scanning densitometers can sequentially measure color bar "patches" comprising color data representative of solids, screened areas, overprints, etc. Through analysis of these color patches, the densitometers can typically be utilized to provide specific density data, in addition to analyzed data such as density differences and the like. Other parameters or quantities which may be obtained through use of scanning densitometers include dot percentage/gain, relative print contrast, trappings, grayness, hue error and various statistical production data.

Known and commercially available scanning densitometer arrangements include apparatus known as the Autosmart TM Densitometer marketed by Cosar Corporation, the Gretag D732 Densitometer marketed by Gretag Limited and the Tobias SCR Densitometer marketed by Tobias Associates, Inc.

The known scanning densitometers typically include relatively complex and large scanning "heads" comprising the electronics and similar apparatus required for optically obtaining color density data. In addition, with a scanning densitometer, the head is typically mounted in a manner so that it is movable along a carriage or the like so as to sequentially obtain color density measurement data from a series of color bar patches positioned on a stationary print sheet. With many of the known scanning densitometers, the scanning heads are continuously in electrical communication with computer processor and memory configurations so as to transmit parameter data and color measurement data between the scanning head electronics and a separate and/or remote computer system. To provide for this electrical communication, many of the known scanning densitometers include cabling interconnections between the scanning head and separate computer-based apparatus.

The electrical cabling required for communication interconnections between the scanning head and separate computer-based apparatus can be of substantial weight. Accordingly, to provide for movement of the scanning head, several known densitometers require relatively complex track, gearing and motor control arrangements for providing the scanning head movement in response to externally initiated commands. The known systems can require a substantial amount of power in view of their motor-driven and cabling characteristics. Also, for purposes of obtaining accurate measurements, many of the known densitometers utilize vacuum systems or other relatively elaborate "hold down" arrangements for purposes of clamping the color bar paper along a flat surface during the measurement cycles. In view of all of the foregoing requirements, many of the known densitometers are also relatively expensive.

SUMMARY OF THE INVENTION

These and other problems of the prior art are overcome in accordance with this invention by means of a densitometer for measuring color characteristics of an object sample under test which comprises an autonomously operating densitometer head movably supported on a transport assembly adjacent the object sample. The densitometer head is connected to an interface unit, which provides an interface to a host computer, only when the head is within a predetermined distance of the interface unit. The autonomous head includes an optical scanner and is responsive to a start signal from the interface unit to move along the transport assembly to generate and store data representative of color characteristics of the object sample and is further responsive to an input signal from the interface unit to transfer stored data to the interface unit. In accordance with one specific embodiment of the invention, signals are transmitted between the interface unit and the autonomous head, when positioned within the predetermined distance of the interface unit, by means of optical couplers in the interface unit and in the head. An electrical connector terminal on the autonomous head and a corresponding terminal on the interface unit provide electrical contact when the head is positioned adjacent the interface unit. The head responds to the start signal, received while positioned within the predetermined distance of the interface unit, by activating an electric motor which propels the head along the transport assembly and away from the interface unit. An internal battery provides the electrical power for the motor and the head includes a charging circuit for charging the battery when the head is connected to the interface unit. Advantageously, in accordance with this invention, a relatively uncomplicated and inexpensive densitometer is provided which avoids the use of electrical cabling required in prior art systems for communications between a stationary computer interface and a moving head.

In accordance with one aspect of the invention, the transport assembly comprises a pair of spaced-apart, substantially parallel transport bars for slidably engaging the autonomously operating densitometer head and a mechanical linkage for raising and lowering the transport bars. Advantageously, an object sample to be tested may be positioned under the transport bars when in a raised position and the transport bars may be lowered to provide a clamp to hold the object sample in a flat position and to bring the densitometer head in close proximity to the object sample. In one specific embodiment of the invention, the mechanical linkage for raising and lowering the transport bars comprises a pair of rotatable shafts, each supporting one of the transport bars, a lever arm attached at each end of each of the shafts, and a pair of links interconnecting pairs of lever arms at opposite ends of the shafts, for concomitantly raising and lowering opposite ends of the support bars. At least one of the support bars is provided with a rack having a plurality of spaced-apart gear teeth and the motor in the densitometer head is provided with a pinion gear for engagement with the gear teeth to provide positive engagement and consistent displacement of the head along the transport assembly for each revolution of the motor.

In accordance with one aspect of the invention, a limit stop is disposed along the transport assembly and a limit switch in the head operated by engagement with the limit stop. Control circuitry in the head is responsive to operation of the limit switch to reverse direction of the motor to cause the head, which is initially moving away from the interface unit, to return to the interface unit. The control circuitry is further responsive to engagement of an electrical connector on the head with a corresponding electrical connector on the interface unit to stop the motor when the head has returned to the interface unit and to transmit a control signal to the host computer via the interface unit.

In accordance with one aspect of the invention, the densitometer head comprises two data memories, one for storing parameter data which may be used in several scanning operations to operate on collected data representative of color characteristics of an object sample under test. Another memory is provided for storing output data for transmission to a host computer upon completion of a scanning operation. Advantageously, the memory for storing parameter data may be a nonvolatile memory which is not affected by interruptions in electrical power.

BRIEF DESCRIPTION OF THE DRAWINGS

The invention will now be described with respect to the drawings, in which.

DESCRIPTION OF THE PREFERRED EMBODIMENT

Figure 2:
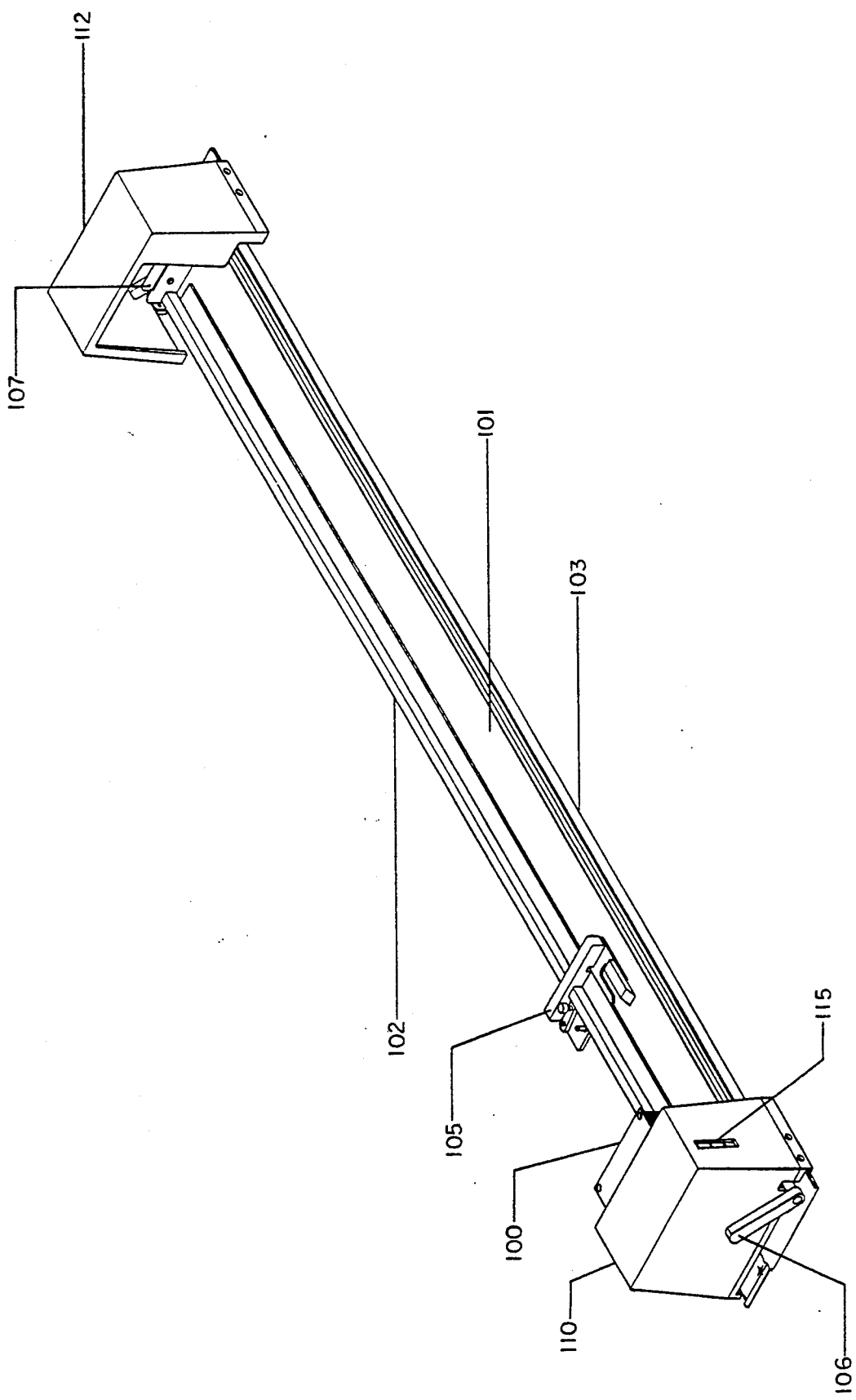
FIG. 2 is a perspective view of a scanning densitometer in accordance with the invention.

The principles of the invention are disclosed, by way of example, in a scanning densitometer as described in subsequent paragraphs herein and illustrated in FIGS. 2-8. FIG. 2 is a perspective view of a scanning densitometer for obtaining color density measurements from colored samples such as color bars commonly used in color printing. The illustrative arrangement of FIG. 2 includes a densitometer head 100 and a densitometer head transport system 101 including a pair of parallel transport bars 102, 103. A sample sheet may be positioned under transport bars 102, 103 and densitometer head 100, which is self-propelled, is adapted to move over the sheet along transport bars 102, 103 up to a distance defined by an end limit stop 105, to obtain color measurement data. Transport bars 102, 103 may be raised and lowered by means of a link mechanism contained within end housings 110 and 112 and operated by lever 106, allowing a sample sheet to be clamped under the bars for measurement purposes. Housing 110 is positioned at one end of parallel transport bars 102, 103, referred to herein as the "docking end." Housing 112 is disposed at the other end of the parallel transport bars 102, 103 and contains link mechanism 107 shown in partial view in FIG. 2 and explained in greater detail with reference to FIG. 3. Operation of lever 106 on housing 110 allows transport bars 102 and 103 to be raised for the purpose of inserting a sheet having a color bar, or the like, to be measured by the densitometer head 100. The housing 110 contains a communication interface for providing an interface to the densitometer head 100 when it is at the docking end in the housing 110. A plurality of cable connectors 115 on housing 110 allow for the provision of electrical power to the densitometer head 100 and provide a control and data transfer interface when head 100 is at the docking end.

Figure 3:
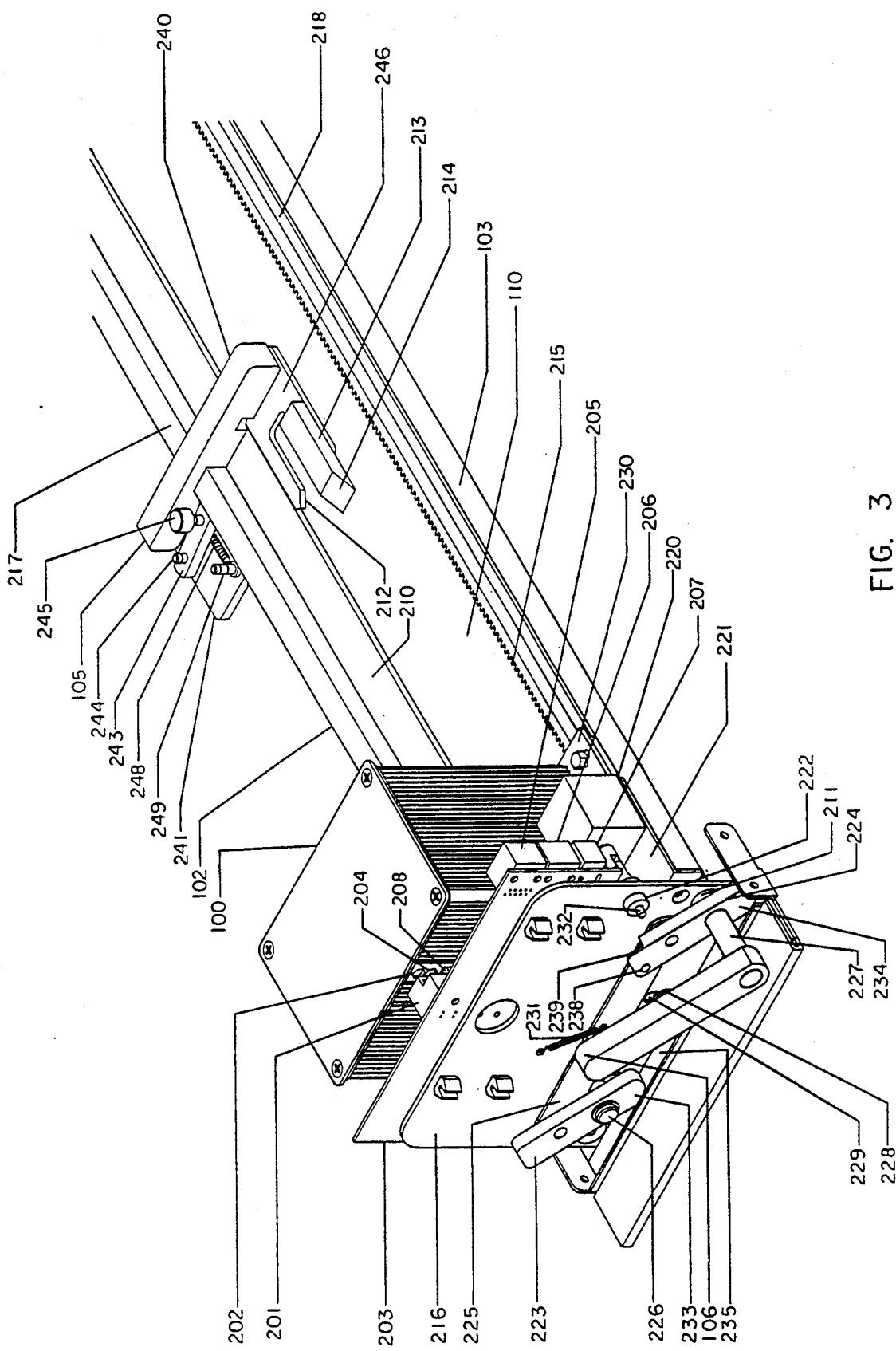
FIG. 3 is a perspective view of the scanning densitometer in accordance with the invention illustrated in FIG. 2, but showing greater detail of the docking end and stop apparatus of the scanning densitometer.

FIG. 3 is a more detailed perspective view of the docking end without the housing cover and of transport bars 102, 103. A printed circuit interface board 203 comprises three cable connectors, 205, 206 and 207, an infrared optical coupler 201 which interfaces with corresponding optical coupler 202, and an electrical connector 208. When densitometer head 100 is docked at the docking end, its optical coupler 202 will be aligned with optical coupler 201, allowing optical signals to be communicated between the interface board 203 and densitometer head 100. Optical couplers 201, 202 are standard well-known devices. Coupler 202 comprises two openings, shown at 204. An optical receiver is aligned, internal to densitometer head 100, with one of the two openings 204 for receiving optical signals and converting the received optical signals to electrical signals for use by electronic circuitry within the densitometer head 100. The other of the two openings 204 is aligned with an optical transmitter, internal to densitometer head 100, which is responsive to electrical signals from circuitry within the densitometer head to generate optical output signals. Optical coupler 201 is similarly provided with two openings (not shown in the drawing). One of the two openings of optical coupler 201 is aligned with the receive opening of optical coupler 202 and includes an optical transmitter responsive to electronic signals received from conductors on interface circuit board 203 to generate optical signals to be received by optical coupler 202. In an analogous fashion, optical coupler 201 has an opening aligned with the transmit opening of optical coupler 202 and includes an optical receiver for converting optical signals received from the densitometer head to electrical signals for transmission on conductors of interface board 203. Connector 205 provides control input from a foot pedal or other control switch and is connected via printed circuit connections (not shown in the drawing) on circuit board 203 to solenoid 220. Connector 206 is similarly connected via printed circuit connections (not shown in the drawing) on board 203 to optical coupler 201 and is used for connection to an associated host computer (not shown in a drawing). Connector 206 may also be connected to solenoid 220 or control of the solenoid from the host computer. Solenoid 220 is mounted on platform 221 attached to plate 216, and at a higher elevation than base plate 230 of densitometer head 100. A standard RS 232 data interface may be used for communications between the densitometer head 100 and the host computer. Connector 207 is an electrical power connector which is used to provide electrical power via circuit board 203 and optical couplers 201 and 202 to a battery charging circuit within the densitometer head 100.

Use of the densitometer in obtaining color density measurements involves downloading certain information defining parameters about the task to be performed, from the host computer to densitometer head 100, via the RS 232 interface connector 206 and optical couplers 201, 202. A color sheet to be measured is placed under the transport bars 102, 103 and one end of the specific area to be examined, for example, the area of the color bars on a printed sheet, is aligned with a pointer on the densitometer head 100. The other end of the area to be examined is aligned with a pointer 212 on the end limit stop 105, and one side of the area to be examined is aligned with alignment bar 210, which is integral to transport bar 102. Thereafter, the parallel transport bars, together with the densitometer head 100, are lowered onto the sheet to be measured by operation of solenoid 220. The transport bars clamp the sheet in place to provide a properly aligned smooth surface for measurement by densitometer head 100. A signal, sent from the host computer to the densitometer head 100 via optical connectors 201, 202, causes an electrical motor internal to the optical densitometer head 100 to be started. The motor is provided with a pinion drive gear engaging teeth of rack 215 on rail 103, so as to move the densitometer head 100 in the direction of the end limit stop 105. The end limit stop 105 is provided with a raised member 213 having an inclined plane 214. A limit switch on the densitometer head 100 is actuated when coming into contact with the inclined plane 214, causing the motor to reverse and the reading mechanism of the densitometer head 100 to be activated. The densitometer head 100 scans the designated area of the aligned sheet as it travels in the direction of the docking end. It collects and stores the color data as it travels, and may perform various computations. After arrival at the docking end, the densitometer head sends a signal via optical couplers 201, 202 to the host computer indicating that the scanning run has been completed. The computer then sends the necessary commands to the head 100 to receive collected and/or computed data. Thereafter, the operator raises the transport system, using the lever 106, so as to remove the sheet.

The mechanism for raising and lowering parallel transport bars 102, 103, together with the densitometer head 100, includes a pair of parallel arms 223, 224 and an interconnecting link 225. A pair of shafts 226, 227 extend longitudinally from the plate 216 and support the transport bars 102, 103. Arms 223 and 224 are attached to shafts 226 and 227, respectively, for rotational engagement, and are provided with curved lower terminal ends 233 and 234, respectively, resting on a base plate 235. The transport bars 102, 103 are shown in a lowered position in FIG. 3. The system may be raised by turning the lever 106 which is attached for rotational engagement with shaft 227. Rotation of shaft 227 in the clockwise direction causes arm 224 to be likewise rotated, and due to the action of link 225, causes arm 223 to be similarly rotated. Rotation of arms 223, 224 causes their curved terminal ends 233, 234, respectively, to be forced against the base plate 235. Base plate 235 is attached to a vertically extending plate 216, and spacer 211 is utilized to position arm 224 a predetermined distance from plate 216.

An alignment pin 228, attached to a horizontally extending bar (not shown in the drawing) interconnecting plate 216, travels in vertically extending slot 229. When arms 223, 224 are rotated in the clockwise direction, their curved terminal ends 233, 234 will slide along base plate 235, causing shafts 226, 227, and hence transport bars 102, 103, to be raised. The opposite ends of transport bars 102, 103 are interconnected by link mechanism 107 contained in housing 112 shown in FIG. 2. The link mechanism 107 comprises a pair of arms corresponding to arms 223, 224 interconnected by a link corresponding to link 225 and resting on a base plate corresponding to base plate 235. The arms of link mechanism 107 are similarly attached to shafts 226 and 227 for rotational engagement. Accordingly, as shaft 227 is rotated, the ends of transport bars 102, 103 disposed in housing 112 are raised and lowered concomitantly with the docking end of the system.

Arm 224 is provided with a reduced section 239 having an opening 238. The reduced section 239 is provided with an inclined plane to facilitate engagement of solenoid pin 232 with arm 224 in a standard fashion. Solenoid pin 232 moves through guide 222 for engagement with opening 238. Solenoid 220 is commonly in the released condition and pin 232 is in an extended position. As arm 224 is moved in a clockwise direction, pin 232 engages opening 238 in arm 224. The solenoid 220 may be operated by means of a control signal from control connector 205 or from host interface connector 206. Operation of solenoid 220 causes pin 232 to be retracted and disengaged from opening 238, thereby releasing arm 224 to allow for rotation in the counterclockwise direction. Arm 224 is biased for counterclockwise rotation by spring 231. In this manner, support arms 102, 103 are lowered upon activation of solenoid 220.

End limit stop 105 comprises a horizontal bar 240 extending in a direction transverse to transport bar 102 and in sliding engagement with transport bar 102. Bar 240 is attached to an adjustment plate 241. An adjustment arm 243, rotationally engaged with plate 241 by means of pivot pin 244 and provided with knob 245, engages transport bar 102 to force sliding horizontal bar 240 in frictional engagement with bar 102. Adjustment arm 243 is attached to spring 248, anchored by pin 249, to force arm 243 against bar 102. Rotation of arm 243 in the counterclockwise direction releases sliding horizontal bar 240 from frictional engagement with transport bar 102. Further attached to bar 240 is horizontal plate 246 of which pointer 212 is an integral part. Attached to plate 246 is raised member 213 provided with an inclined plane 214 for engagement with the densitometer head 100 to define the limit of travel of the head 100.

Figure 4:
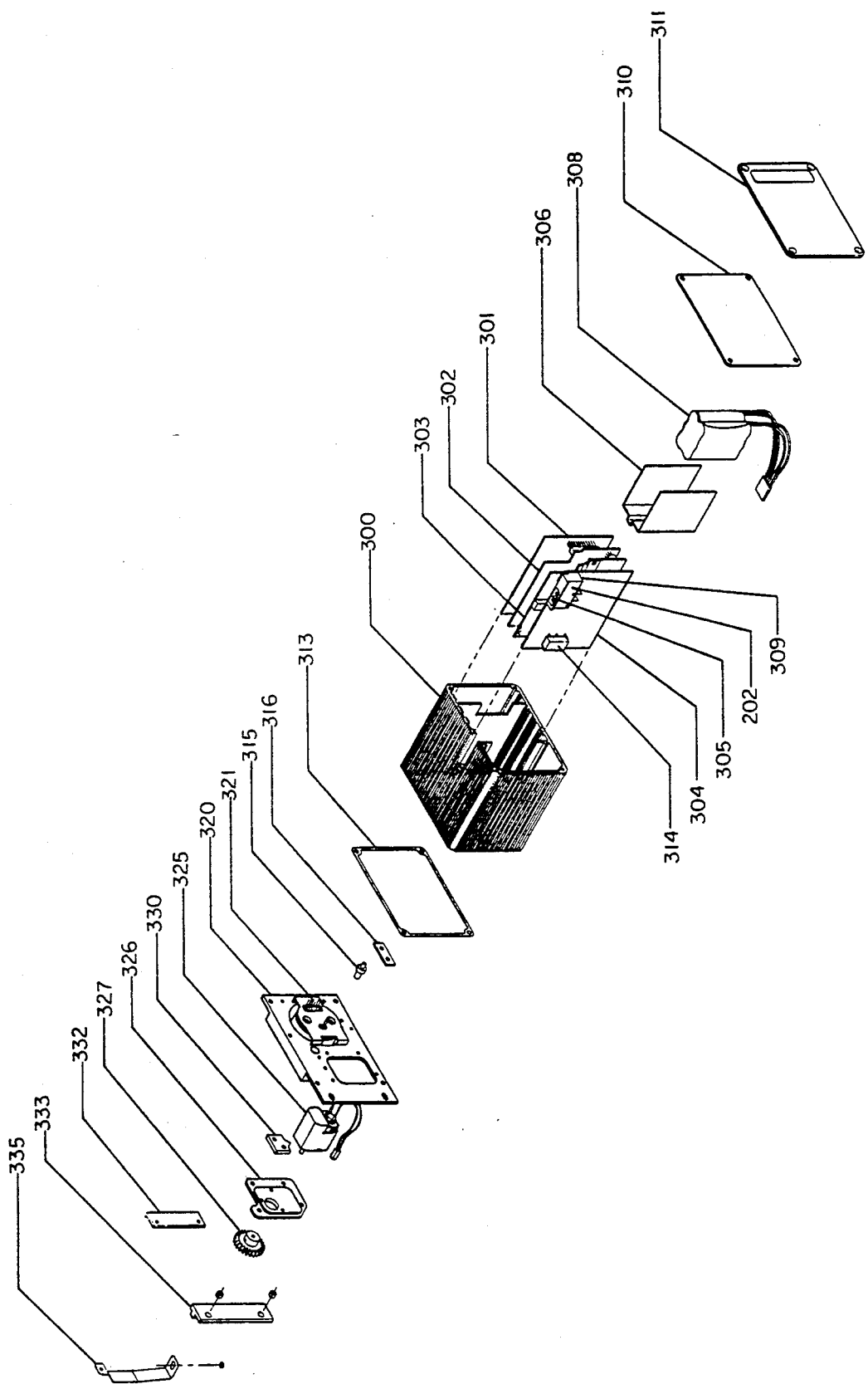
FIG. 4 is an exploded view of the densitometer head of the scanning densitometer in accordance with the invention shown in FIGS. 2 and 3.

FIG. 4 is an exploded view of the densitometer head 100 shown in FIGS. 2 and 3. Shown in FIG. 4 is the densitometer housing 300 in which a number of printed circuit boards 301 through 304 are supported. The circuit boards each contain a number of electrical components which will be described in greater detail later herein with reference to FIG. 6. Shown on circuit board 304 is housing 309 containing optical coupler 202 and electrical connector 208, referred to earlier herein with respect to FIG. 3. Further shown on circuit board 304 is a limit switch 314 which, when actuated, serves to reverse the direction of travel of the densitometer. A switch pin 315 and switch pin stop 316 cooperate to actuate limit switch 314 when pin 315 engages the inclined plane 214 of the end limit stop 105 depicted in FIG. 3. A battery 308 is contained within a battery shield 306 within the housing 300 to provide electrical power for motor 325 and electronic circuitry of circuit boards 301 through 304. Cover 311, together with cover seal 310, form the top cover for housing 300.

Figure 5:
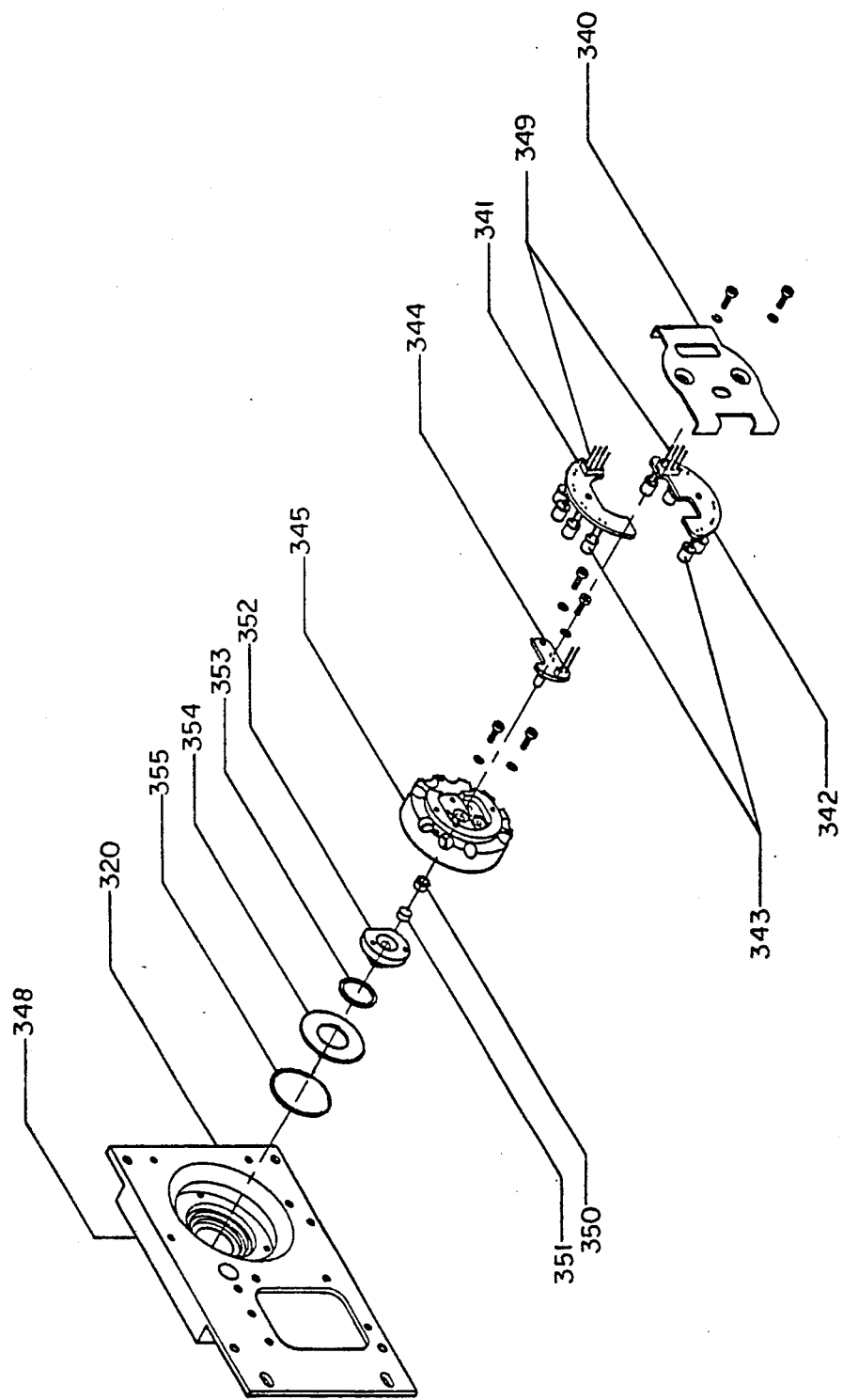
FIG. 5 is a partially exploded view of portions of the optical elements associated with the scanning densitometer in accordance with the invention illustrated in FIGS. 2-4.

Bottom plate 320 houses the nosepiece 321 containing the necessary optical elements required for optical scanning, and described in further detail with respect to FIG. 5. A motor mounting plate 326 attaches to bottom plate 320 and provides for the mounting of motor 325, to which pinion gear 327 is attached. A pointer 330, which attaches to the bottom plate 320, is used for alignment of an area to be optically measured as described earlier herein. Pointer 330 extends beyond housing 300 so as to be clearly visible for aligning the area to be measured with the pointer. Slides 332, 333 are attached to opposite ends of the bottom plate 320 and are in sliding engagement with housings 217, 218 when the densitometer head 100 is positioned on the transport bars 102 and 103. A pressure spring 235 is mounted on the bottom plate 320 to apply pressure to the area on which color measurements are to be made, as densitometer head 100 moves along transport bars 102, 103, propelled by motor 325 by means of engagement of pinion gear 327 with teeth of rack 215 of transport bar 103.

Figure 1:
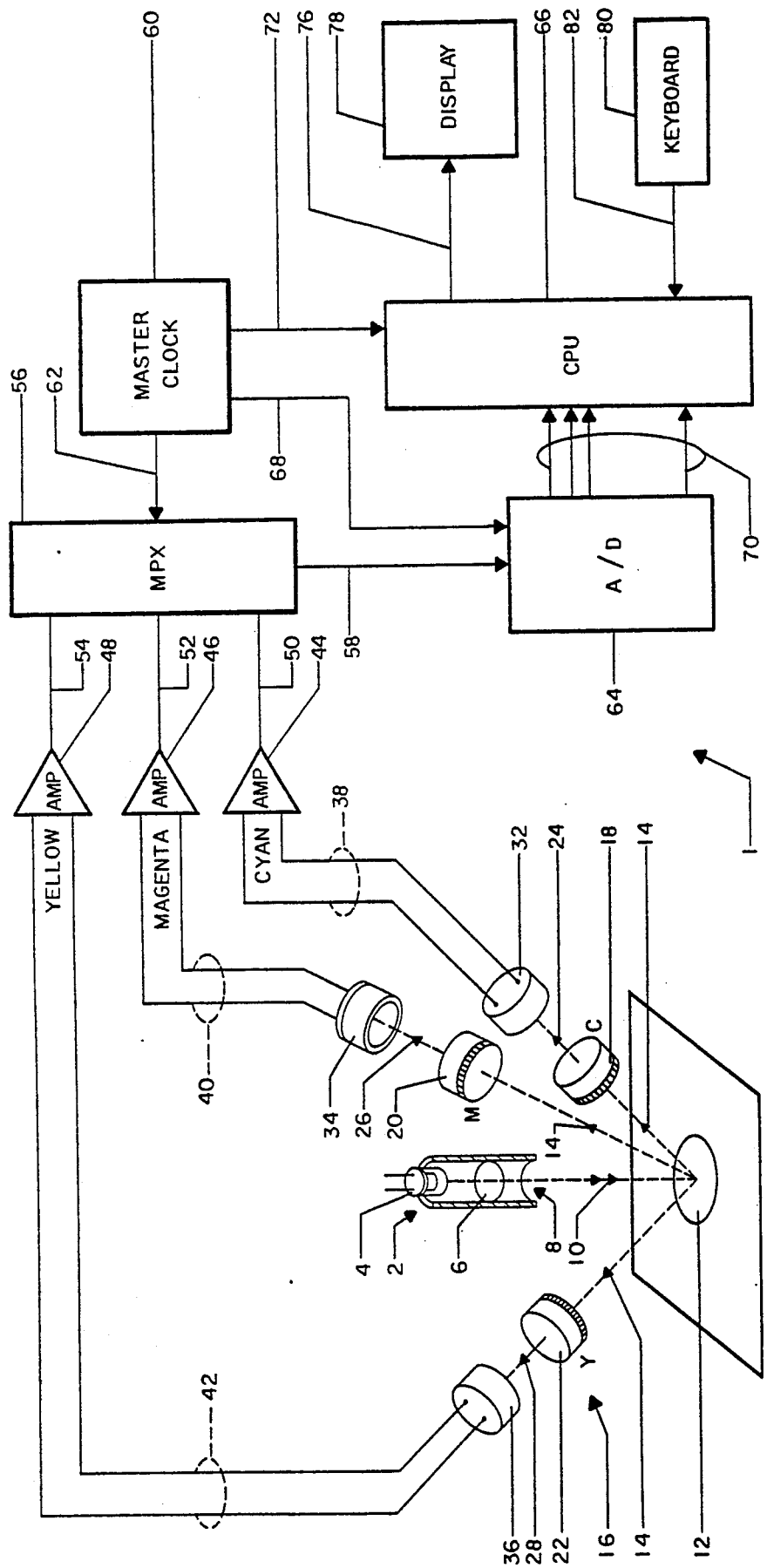
FIG. 1 is a prior art illustration of a partially schematic block diagram of a densitometer apparatus for measuring color densities.

It is well known in color technology to measure color density of, for example a color bar strip of a color printed sheet, by illuminating such a color bar strip by means of a light source and sensing reflected light by means of sensors provided with filters to detect three basic color shades such as cyan, magenta, and yellow. Color density measurements are made on the basis of the strength of the reflected light within the bandwidth defined by the three selected color shades. It is also known to sense the intensity of the light source in order to be able to take into consideration the variations in the intensity of the light source in making color density measurements. The optical nose piece assembly 321, shown in exploded view in FIG. 5, contains a light source 344 and a plurality of reflective light sensors 343 which are provided with filters to detect the cyan, magenta, and yellow color shades. Side sensors are provided to measure the intensity of the light source. The light sensors 343 are mounted on circuit boards 341 and 342, and electrical analog signals generated by the sensors are transmitted via pins 349 to one of the circuit boards 301 through 304. Circuit boards 341 and 342, together with sensors 343 and light source 344, are mounted in an optic housing 345. The optic housing 345, together with an inner aperture 350, a lens 351, an outer aperture 352, an inner optical seal 353, infrared glass 354, an outer optic seal 355, and optical shield 340 are retained in bottom plate 320 and housing extension 348. The nosepiece assembly 321 and its various component parts are well known in the industry and are commercially available. Greater detail of the concepts associated with optics and electronics components associated with the measurement of color densities is described in the section entitled "Background of the Invention" with respect to FIG. 1.

Figure 6:
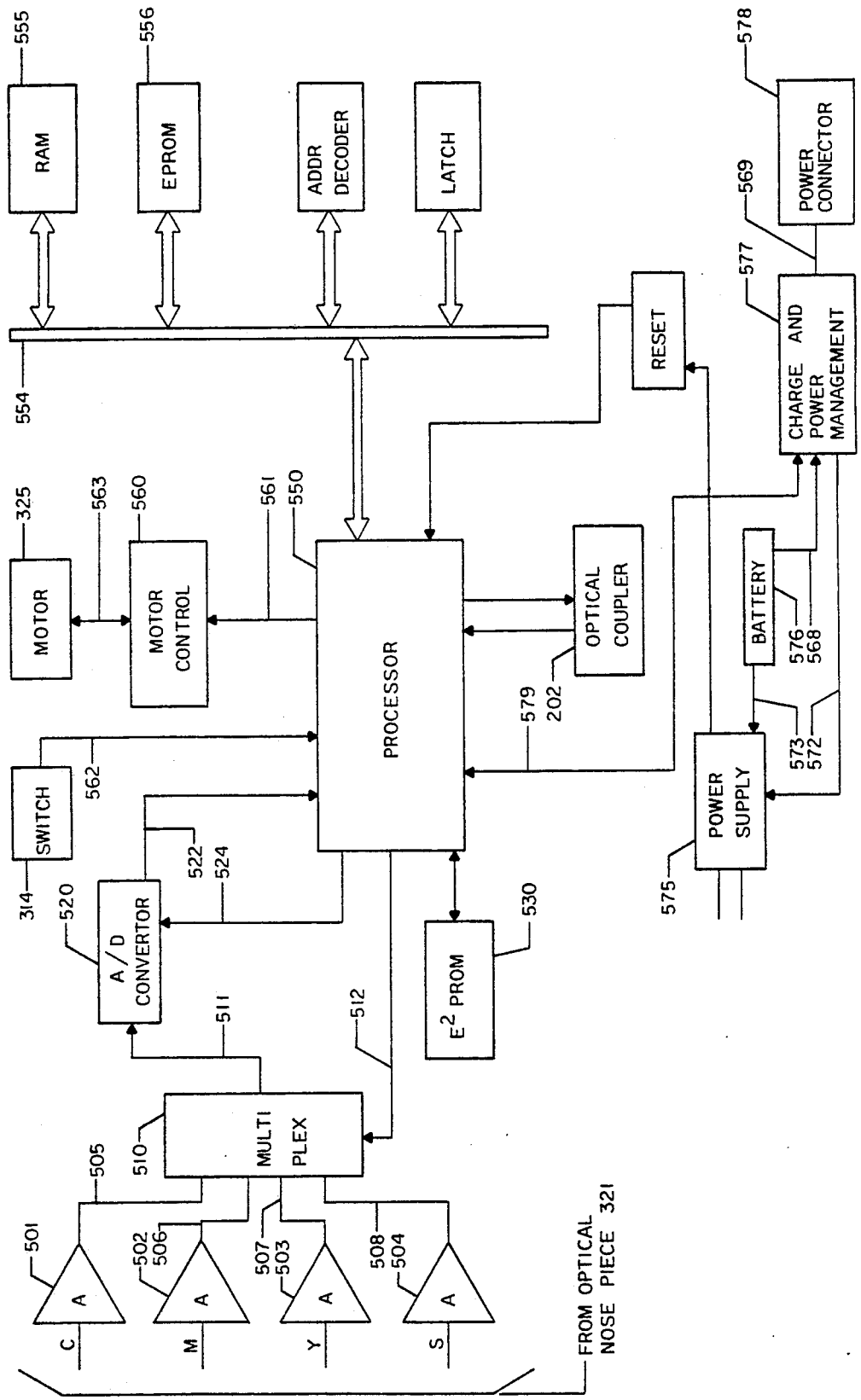
FIG. 6 is a block diagram representation of certain of the circuitry of the scanning densitometer shown in FIG. 2.

FIG. 6 is a block diagram representation of certain of the circuitry on circuit boards 301 through 304 of FIG. 4. FIG. 6 shows a plurality of input leads labeled C, M, Y, and S. These four inputs represent electrical signals from the optical nose piece 321 defining the cyan, magenta, and yellow light intensities and a side sensor output representing intensity of the light source. The C, M, Y, and S signals are each amplified by means of conventional amplifiers 501 through 504 which amplify the relatively low level output signals from the respective sensors to output signals compatible with signal levels used in multiplex circuit 510. Output signals from amplifiers 501 through 504 are transmitted to multiplex circuit 510 via conductors 505 through 508, respectively, where the four separate signals are converted to a serial stream of analog signals and transmitted via conductor 511 to an analog-to-digital convertor 520. The multiplexed analog signals received from multiplexer 510 are sampled and converted into digital data representative of the analog signals, by means of convertor 520. A serial stream of digital data bits representing the signals corresponding to the outputs of the cyan, magenta, and yellow color sensors as well as the optical source sensor, are transmitted from convertor 520 to a processor 550 by means of conductor 522.

Figure 7:
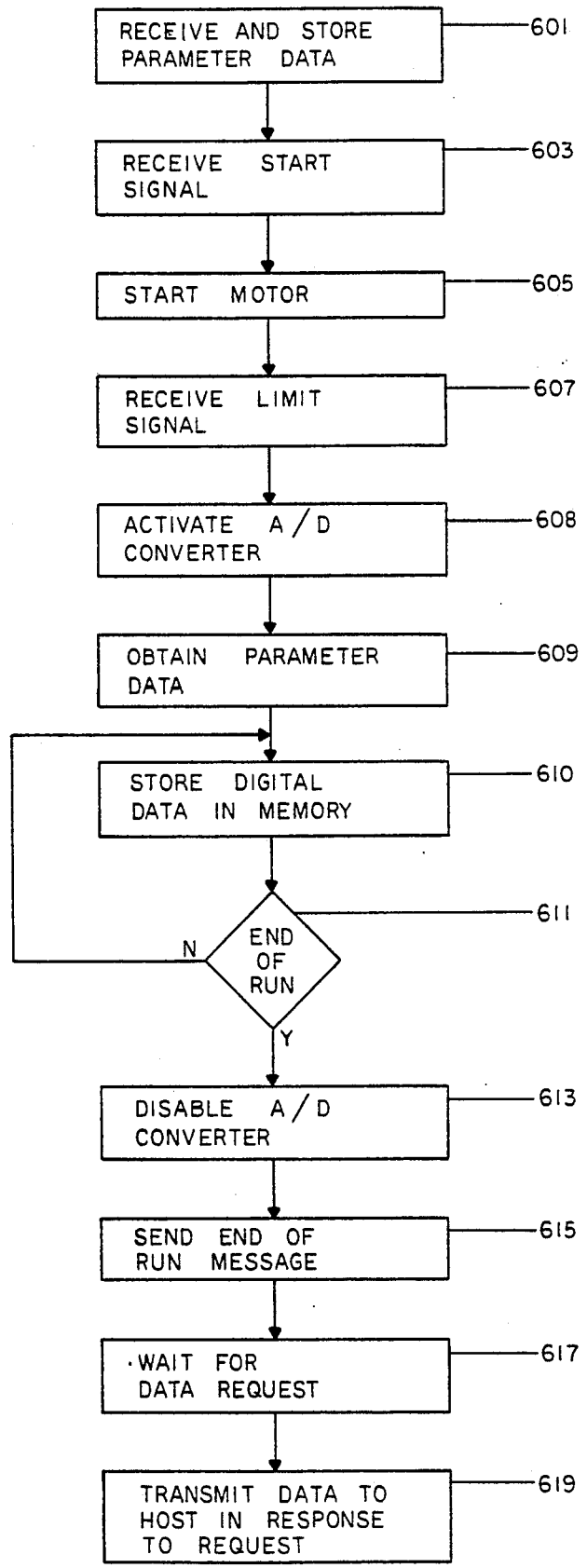
FIG. 7 is a sequence diagram of certain of the functions performed by the processor apparatus of the scanning densitometer shown in FIG. 2 in accordance with the invention.

The processor 550, which may be a standard commercially available microprocessor, such as the Intel 80C196, controls movement of densitometer head 100 and collects and stores data, as generally outlined in flow chart form in FIG. 7. As discussed earlier herein, reading of a color bar strip or the like is initiated by an operator aligning the area to be read by means of a pointer 330 on the densitometer head 100, pointer 212, and alignment bar 210. Thereafter, the operator may notify the host computer by touching appropriate keys of a keyboard or the like. The host can actuate solenoid 220, to lower the transport bars 102, 103, together with the densitometer head 100 onto the sheet of material to be scanned. The densitometer head 100 is positioned at the docking end prior to the taking of measurements and optical couplers 201 and 202 will be aligned when head 100 is in the lowered position, allowing communication between head 100 and the host computer. The host computer, which is connected to interface board 203 via RS 232 connector 206, may be a system computer using the densitometer output for feedback control or the like or may be an AT style computer with a monitor to provide a stand-alone densitometer system. A host to densitometer interface such as disclosed in U.S. Pat. No. 4,591,978 to S. H. Peterson et al may be employed in communications between the host processor and the densitometer head 100.

The host computer may download to the densitometer head 100 certain information such as color bar patch width, color bar length, and other measurement parameter data. Receiving and storing parameter data by the densitometer head 100 is indicated in block 601 of FIG. 7. Such information may, for example, be stored in an electronically erasable memory 530, directly connected for read and write access to processor 550. The less volatile, electronically erasable memory is used for the parameter data since that data may be useful for an extended period of time over many runs. After transmission of the necessary data to densitometer head 100, the host computer provides a start signal transmitted via optical couplers 201, 202. Receipt of this start signal is indicated in block 603 of FIG. 7.

Having received the start signal, processor 550 provides a corresponding indication to motor control 560 via conductor 561, which in turn provides an appropriate signal to motor 325, as reflected in block 605 of FIG. 7. This causes the motor 325 to move the densitometer head 100 along transport bars 102, 103 by engagement of pinion gear 327 with teeth of rack 215 on transport bar 103. Motor 325 may be a standard small electric motor. In one preferred embodiment, the motor propels the head 100 at the rate of four inches per second. Starting of the motor 325 propels the densitometer head 100 in the direction of the end limit stop 105, away from the docking end of the transport system, "breaking" all connection to the host. Consequently, no further communication takes place between the densitometer head 100 and the host processor until it returns to the docking end. Accordingly, the densitometer head 100 operates autonomously during the color measuring operation.

Densitometer head 100 travels toward stop 105 until switch pin 315 of the densitometer head 100 engages inclined plane 214. At that point, switch 314 is actuated and sends a signal to processor 550 via conductor 562, as reflected in block 607 of FIG. 7. Processor 550 transmits a control signal to motor control 560 via conductor 561 to reverse the direction of motor 325. A corresponding reversing signal is applied to motor 325 from motor control 560 via conductor 563. The densitometer head 100 is now prepared to begin reading color data from a color bar strip positioned under transport bars 102, 103. Accordingly, the analog-to-digital convertor 520 is initialized and enabled via conductor 524, as indicated in block 608 of FIG. 7. Processor 550 enables and initializes multiplexer 510 via conductor 512 and convertor 520 via conductor 524 on the basis of the parameter data. Processor 550 receives a tachometer signal from motor control 560 via conductor 561. The tachometer signal is derived by motor control 560 on the basis of a back EMF signal obtained from motor 325 via conductor 563. The tachometer signal is used by processor 550 together with the parameter data, obtained as indicated in block 609, to process the data received from convertor 520 and store the processed data in random access memory 555, as indicated in block 610. The parameter data may simply be used to define the manner in which the data will be stored and later presented to the host processor.

Alternatively, additional data processing functions may be defined for processor 550 on the basis of the received parameter data, such as pattern recognition. Pattern recognition algorithms for use in the computation of color density measurements are known in the art. One particular such algorithm is described in U.S. Pat. application Ser. No. 478,475, filed Feb. 12, 1990, in the names of Peterson et al, which is hereby incorporated by reference. The extent of the processing to be done in the densitometer head is clearly a function of the capabilities of the processor 550 and the programs for the processor as stored, for example, in program memory 556. Program memory 556 will include instructions for processor 550 needed to execute its various functions, such as those outlined in block diagram form in FIG. 7.

Processor 550 will continue to process the sensor output data received from the analog digital convertor 520 until densitometer head 100 has reached the end of its run. As indicated in block 611 in FIG. 7, a test is made periodically by processor 550 to determine whether the end of the run has been reached. The end-of-run is detected when power connector 208, shown in FIG. 3, makes contact with a corresponding connector 305, shown in FIG. 4, of densitometer head 100. When that occurs, charge and power management circuit 577 sends an arrival signal to processor 550 via conductor 579. If the end-of-run has not yet occurred, the processor 550 will continue to receive and store digital data from convertor 520. When the end of run has occurred, processor 550 will disable convertor 520 and discontinue storing data in memory as indicated in block 613 of FIG. 7. When the densitometer head 100 has arrived at the docking end at the end of the run, optical coupler 202 is once again aligned with optical coupler 201 so that the messages can be transmitted between densitometer head 101 and the host computer. An end-of-run message is sent by processor 550 via optical coupler 202 when the end-of-run signal has been received, as indicated in block 615 of FIG. 7. Thereafter, processor 550 waits for a request for data from the host computer as indicated in block 617, and when the request has been received, run data stored in the random access memory 555 is transmitted via optical coupler 202, optical coupler 201 and host interface 206 to the host computer. As indicated earlier, upon completion of a run the operator may raise the transport bars 102, 103 by operation of lever 106, remove the sheet that has been measured and insert a new sheet to repeat the operation.

Figure 8:
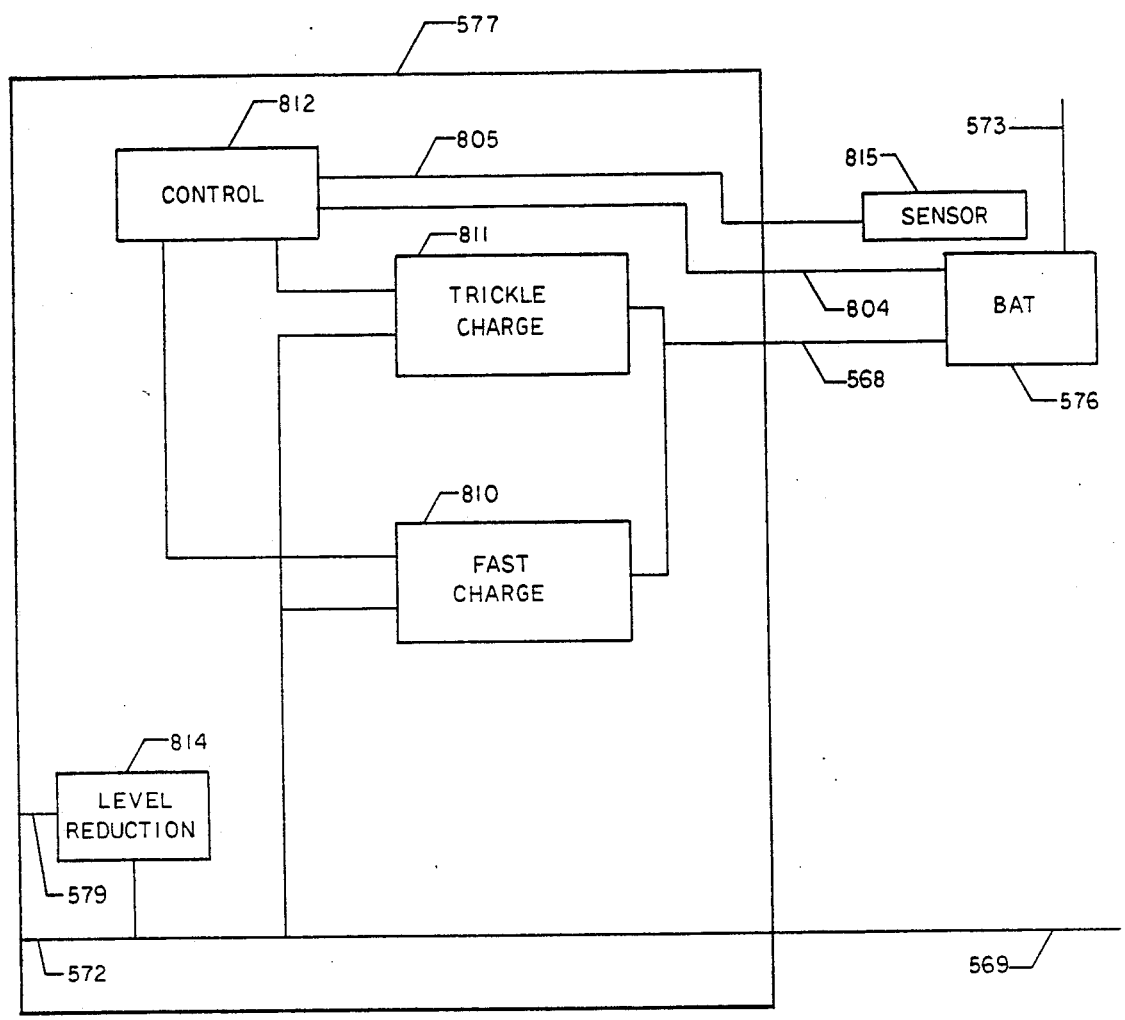
FIG. 8 is a block diagram illustration of certain of the charge and power management circuit of the scanning densitometer shown in FIG. 2.

It will be understood that each of the electronic circuits, including processor 550, motor 325, and other circuits and electrical devices require electrical power and certain circuits require periodic timing pulses. The timing pulses are provided as needed, by means of a system clock in a well-known fashion, and need not be described herein. A power supply circuit 575 provides electrical power at various current and voltage levels to meet the various requirements of the system of densitometer head 100. The power supply circuit 575 receives electrical power from battery 576 via conductor 573 when disengaged from the docking end power connector 208. When densitometer head 100 is positioned in the docking end, electrical power is provided from power connector 208 to charge and power management circuit 577 via power connector 578 and conductor 579. When densitometer head 100 is in the docked position, power supply circuit 575 receives its power from the charge and power management circuit 577, which charges battery 576. FIG. 8 is a diagrammatic representation of the charge and power management circuit of 577. Circuit 577 comprises a control 812 which is connected to battery 576 by means of conductor 804 to sense the battery voltage level. When that level is below a certain value, e.g., 6.25 volts, the control 812 activates a fast-charge circuit 810 which is connected to conductor 569 from the power connector 578. The fast-charge circuit 810, upon activation, provides a fast charge to battery 576 via conductor 568. A thermal sensor 815 is positioned near battery 576 and provides a signal to control 812 via conductor 805 when the sensor senses a battery temperature in excess of a predetermined value, e.g., 45° C. When that temperature is sensed, control 812 disables the fast-charge circuit 810 and enables a trickle charge circuit 811 to provide a trickle charge on conductor 568 to battery 576. In this manner, a high battery charge is maintained within battery 576 to operate the densitometer head 100 when away from the docking end. The charge and power management circuit provides power to power supply 575 via conductor 572 when the densitometer head 100 is in the docked position. A level reduction circuit 814 is used to transmit a signal to processor 550 on conductor 579 when the power connector 578 is in contact with the corresponding power connector 208 on interface board 203. The level reduction circuit 814 is connected to conductor 569 from power connector 578 and provides a reduced level signal on conductor 579 to processor 550, indicating that the docking position has been reached.

It will be further understood that the embodiments described herein are illustrative of the principles of this invention and that numerous variations thereof may be devised by those skilled in the art without departing from the spirit and scope of this invention.

The embodiments of the invention in which an exclusive property or privilege is claimed are defined as follows:

1. A densitometer for measuring color characteristics of an object sample under test, comprising:
an autonomously operating densitometer head comprising scanning means for generating electrical output signals representative of color characteristics of a scanned sample, memory means, control means for storing data representative of said electrical output signals in said memory means, optical coupler means for transmitting and receiving optical signals, an electrical power source and means connectable to an electrical connector for charging said power source;
a densitometer support arrangement comprising a pair of essentially parallel transport bars for slidably supporting said densitometer head, stop means disposed along said transport bars, means for raising and lowering said transport bars including a pair of rotatable shafts supporting said transport bars and a plurality of lever arms attached at each end of said shafts and a pair of links for interconnecting pairs of said lever arms at opposite ends of said shafts for concomitantly raising and lowering opposite ends of said transport bars;
communication interface means mounted in proximity of one end of said transport bars and comprising means for connection to a host computer and interface optical coupler means responsive to electrical signals from said host computer to transmit optical signals and responsive to received optical signals to transmit electrical signals to said host computer;
said densitometer head further comprising drive means engaging at least one of said transport bars, said control means responsive to an optical signal received via said optical coupler to control said drive means to move said densitometer head along said transport bars in the direction of said stop means, said control means responsive to electrical output signals from said scanning means for storing data representative of electrical signals representing color density readings obtained from said scanner while said densitometer head is moved along said transport bars, means responsive to detection of proximity of said limit stop to control said drive means to move said densitometer head toward said one end of said transport bars and means for detecting proximity of said one end of said transport bars, said control means responsive to detection of said one end of said transport bars for transmitting an optical signal to said optical coupler and responsive to an optical signal from said interface optical coupler to transmit optical signals representative of said stored data.

2. A densitometer for measuring color characteristics of an object sample under test, comprising:
an autonomously operating densitometer head comprising an optical scanner for generating output data representative of color characteristics of an object sample exposed to said scanner and memory means for storing said output data;
a longitudinally extending transport assembly for movably supporting said densitometer head adjacent an object sample;
an interface unit disposed adjacent said assembly for connection to a host computer and for transmitting and receiving signals;
a connector device for providing a signal transmission connection between said head and said interface unit when said head is disposed within a predetermined distance of said interface unit;
said densitometer head further comprising an electric motor for propelling said head along said assembly for exposing said object sample to said optical scanner, control circuitry responsive to a star signal received via said connector device for activating said motor and circuitry responsive to an input signal received via said connector device to transmit data stored in said memory means to said interface unit via said connector device.

3. The densitometer in accordance with claim 2 wherein said connector device comprises an optical coupler on said interface unit and an optical coupler on said head, each for optically transmitting and receiving signals only when said head is within said predetermined distance of said interface unit.

4. The densitometer in accordance with claim 2 wherein said connector device comprises an electrical connector terminal on said head and an electrical connector terminal on said interface unit and said connector terminals are electrically connected only when said head is within said predetermined distance of said interface unit.

5. The densitometer head in accordance with claim 4 wherein said head further comprises a battery for providing electrical power for said head when said head is removed from said interface unit by a distance greater than said predetermined distance.

6. The densitometer in accordance with claim 5 wherein siad head further comprises a charging circuit connected to said electrical connector terminal on said head for charging said battery when said head is within said predetermined distance of said interface unit.

7. The densitometer in accordance with claim 2 wherein said transport assembly comprises a pair of spaced-apart, substantially parallel transport bars disposed in a substantially horizontal plane extending over an object sample under test for slidably supporting said densitometer head over an object sample under test.

8. The densitometer in accordance with claim 7 wherein said motor engages at least one of said transport bars.

9. The densitometer in accordance with claim 8 wherein said at least one bar comprises a rack having a plurality of spaced-apart gear teeth and said motor comprises a pinion gear for engagement with said gear teeth.

10. The densitometer in accordance with claim 7 wherein said transport assembly further comprises a mechanical linkage for raising and lowering said transport bars.

11. The densitometer in accordance with claim 10 wherein said transport assembly comprises a pair of rotatable shafts, each supporting one of said transport bars, a plurality of lever arms, one attached at each end of each of said shafts and each having a support end for slidably engaging a support surface, and a pair of links interconnecting pairs of said lever arms at opposite ends of said shafts, whereby opposite ends of said support bars are concomitantly raised and lowered relative to said support surface when one of said shafts is rotated.

12. The densitometer in accordance with claim 2, and further comprising a limit stop disposed along said transport assembly, wherein said interface unit is disposed at one end of said transport assembly and wherein said head comprises a limit switch operated by engagement with said limit stop and said control circuitry is responsive to said start signal for activating said motor to propel said head in a direction away from said interface unit and responsive to operation of said limit switch to reverse direction of said motor, whereby said head is initially moved away from said interface unit and is moved toward said interface unit after contact with said limit stop.

13. The densitometer in accordance with claim 12 wherein said connector device comprises electrical connector terminals on said head and on said interface unit and said control circuitry in said head is responsive to engagement of said connector terminals for stopping said motor.

14. The densitometer in accordance with claim 13 wherein said control circuitry is further responsive to engagement of said connector terminals for transmitting a control signal via said connector device and said interface unit to said host computer.

15. The densitometer in accordance with claim 2 wherein said densitometer head comprises two data memories and is responsive to the receipt of parameter data from said interface unit for storing said parameter data in a first of said memories and is responsive to receipt of said optical scanner output data for storing said optical scanner output data in a second of said memories.

16. The densitometer in accordance with claim 15 wherein said densitometer head comprises circuitry for reading said parameter data and performing data processing operations on said optical scanner output data in accordance with said parameter data prior to storing said output data in said second memory.

17. A method of measuring color characteristics of an object sample under test in a system having a host processor and a movable densitometer head, comprising the steps of:

positioning an object sample in a predetermined area;
transmitting parameter data from the host computer to the densitometer head;
moving the densitometer head adjacent the object sample;
detecting information representative of color characteristics of the sample and storing the information in the densitometer head;
detecting an end-of-run condition in the densitometer head; and
initiating transfer of stored data from the densitometer head to the host processor in response to detection of the end-of-run condition.

18. The method of claim 17 and further comprising the step of detecting a distant end limit prior to the step of detecting and storing information.

19. The method of claim 17 wherein the step of initiating a transfer of stored data comprises the steps of transmitting an end-of-run message to the host processor, waiting for a data request and transmitting the stored data to the host processor in response to receipt of the data request.

* * * * *

UNITED STATES PATENT AND TRADEMARK OFFICE
CERTIFICATE OF CORRECTION

PATENT NO. : 5,073,028

DATED : December 17, 1991

INVENTOR(S) : DAVID R. BOWDEN et al.

It is certified that error appears in the above-identified patent and that said Letters Patent is hereby corrected as shown below:

```
Column 18, claim 2, line 53:
    "said assembly" should be --said transport assembly--;

Column 18, claim 2, line 55:
    "star" should be --start--;

Column 19, claim 6, line 12:
    "siad" should be --said--.
```

Signed and Sealed this

Thirtieth Day of March, 1993

Attest:

STEPHEN G. KUNIN

*Attesting Officer*  Acting Commissioner of Patents and Trademarks